United States Patent [19]
Mammone

[11] Patent Number: 5,818,957
[45] Date of Patent: *Oct. 6, 1998

[54] PROCESSING OF KERATOSCOPIC IMAGES

[75] Inventor: Richard J. Mammone, Bridgewater, N.J.

[73] Assignee: Computed Anatomy Incorporated, New York, N.Y.

[*] Notice: The term of this patent shall not extend beyond the expiration date of Pat. No. 5,796,859.

[21] Appl. No.: 44,104

[22] Filed: Apr. 8, 1993

Related U.S. Application Data

[63] Continuation of Ser. No. 773,679, Oct. 8, 1991, abandoned.

[51] Int. Cl.$^6$ ........................................................ G06K 9/00
[52] U.S. Cl. ............................ 382/128; 351/212; 351/221
[58] Field of Search ............................ 382/6, 1, 43, 128; 356/376; 351/212, 247, 206, 221

[56] References Cited

U.S. PATENT DOCUMENTS

| | | | |
|---|---|---|---|
| 3,598,478 | 8/1971 | Townsley | 351/212 |
| 3,797,921 | 3/1974 | Kilmer et al. | 351/206 |
| 4,685,140 | 8/1987 | Mount, II | 382/128 |
| 4,772,115 | 9/1988 | Gersten et al. | 351/212 |
| 4,794,550 | 12/1988 | Greivenkamp, Jr. | 356/376 |
| 4,805,129 | 2/1989 | David | 382/54 |
| 4,863,260 | 9/1989 | Gersten et al. | 351/212 |
| 4,978,213 | 12/1990 | El Hage et al. | 351/212 |
| 4,995,716 | 2/1991 | Warnicki et al. | 351/212 |
| 5,054,907 | 10/1991 | Sklar | 351/212 |
| 5,110,200 | 5/1992 | Snook | 351/212 |

FOREIGN PATENT DOCUMENTS

WO9201417 2/1992 WIPO.

OTHER PUBLICATIONS

Takeda et al., Fourier–Transform Method of Fringe–Pattern Analysis for Computer–Based Topography and Interferometry, J. Opt. Soc. Am, Jan. 1982, pp. 150–160, vol. 72, No. 1.

Tribolet, José M., A New Phase Unwrapping Algorithm, IEEE Transactions on Acoustics, Speech and Signal Processing, vol. ASSP–25, No. 1, Apr. 1977 pp. 170–177.

Takeda et al., "Fourier Transform Profilometry for the Automatic Measurement of 3–D Object Shapes", Applied Optics 22;3977–82, Dec. 15, 1983.

Suganuma et al., "Three Dimensional Shape Analysis by Use of a Projected Grating Image", Optical Engineering, 30:1529–33, Oct. 1991.

*Primary Examiner*—Leo H. Boudreau
*Assistant Examiner*—Bhavesh Mehta
*Attorney, Agent, or Firm*—Fish & Richardson P.C.

[57] ABSTRACT

Processing of the two-dimensional image of a three-dimensional object, such as the human cornea, that has been illuminated with a structured light pattern. A specially filtered Fourier transform and inverse transform are processed to yield the instantaneous spatial frequencies of the illuminated pattern. The instantaneous spatial frequencies are mapped to the instantaneous dioptric powers or depth coordinates of the object's surface.

13 Claims, 5 Drawing Sheets

PROCESSING OF KERATOSCOPIC IMAGES

This application is a continuation of application Ser. No. 07/773,679 filed Oct. 8, 1991, now abandoned.

TECHNICAL FIELD

This invention relates to instruments for measuring surface topography, and more particularly, to such instruments known as keratoscopes.

BACKGROUND OF THE INVENTION

As shown in U.S. Pat. Nos. 3,598,478 to Townsley and 4,772,115 to Gersten et al., mapping an object's surface may require that the surface be illuminated with a known pattern of light, sometimes referred to as "structured light". The light pattern used may be chosen to take advantage of the principle anticipated surface feature. Where the surface is grossly spherical, such as the human cornea, concentric circular light rings are often used. As shown in the Warnicki et al. U.S. Pat. No. 4,995,716 the structured light may be obtained using linear Ronchi rulings projected on the cornea from a photographic mask source by first making the surface of the cornea diffuse to blue light through the use of fluorescein drops. Corneal topography is ascertained by measuring the shift in position of the light band edges from their expected position for a flat surface.

If the surface is specular, however, a real image cannot be obtained from the surface. Apparatus employing Placido disc devices rely on capturing the structured light image reflected from the specular corneal surface. However, the light reflected from a specular surface depends on the angle between the incident ray and the normal of the surface at the point of incidence. The basic Placido disc contains a series of illuminated rings positioned at some distance from the cornea. To have rings cover more than the central portion of the cornea it is necessary that the diameter of the Placido disc be significantly larger than that of the cornea.

An alternate form of Placido disc device is shown in Gersten et al. U.S. Pat. No. 4,772,115 in which a series of illuminated rings that are spaced in a mathematically pre-determined manner are displayed along the length of a plastic cylinder one end of which is positioned close to the eye. The spacing of the rings along the cylinder, is chosen so that the structured light pattern reflected from a perfectly spherical specular surface will appear as a series of equally spaced rings.

The apparatus of the aforementioned Warnicki et al. '716 patent and that shown in Gersten et al. U.S. Pat. No. 4,863,260 disclose computer-controlled corneal mapping systems for providing quantitative information about the corneal topography. However, both systems require that all of the edges of the structured light pattern be ascertained. This requires considerable image processing, as does compensating for the several kinds of artifacts that may appear in the image. From the edge information the "X" and "Y" coordinates of a point on each detected light band is determined and from these points curve-fitting algorithms are employed to re-construct the corneal topography. In fitting line segments to the points, decisions are made regarding which points to discard as artifacts according to predetermined formulae, such as the simplex algorithm.

The technique disclosed in the aforementioned Warnicki et al. U.S. Pat. No. 4,995,716 is applicable only to diffuse surfaces because the shift in the position of the light band edges from their expected position for a flat surface is dependant solely on the distance of the surface being mapped from the ideal plane and not on the angle of the surface. For a specular surface, however, the light reflected from the surface to be mapped also depends on the angle between the incident light ray and the normal to the surface. Moreover, the technique of the '716 patent does not eliminate the need to locate the edges of each of the Ronchi rulings and, accordingly, much image processing is required. The concept of what is an "edge" is itself a concept that is easily mired in definitional abstraction.

Once the formulae of the line segments connecting the detected "edge" points are known, a number of further calculations must be performed to relate the observed two-dimensional line pattern to the actual degree of curvature present at each portion of the corneal surface. In ascertaining the location of the line segments, the distortion introduced by the magnification effect of the specular corneal surface must be counteracted. The effect of this magnification must be taken into account in calculating the surface geometry from the apparent position of the line segments.

In order to provide such "real-time" quantitative information about the geometry of the corneal surface as would be desired, for example, by an ophthalmic surgeon during the course of an operation, it would be desirable to reduce the amount of time taken in such image processing activities as edge detection and compensation for optical distortions.

SUMMARY OF THE INVENTION

I have discovered that quantitative information about the refractive powers exhibited over the corneal surface can be obtained in a faster and more accurate fashion than has heretofore been possible. In accordance with my method it is no longer necessary to use processing time to detect all of the light band edges. I have taken advantage of the various ways in which the spacing of the bands in the light pattern appearing on the surface varies with the distance between the source of the structured light pattern and the surface, taking into account whether the surface is specular or diffuse and whether the light pattern of the mask source is itself equally spaced or is designed to illuminate a particular surface with an equally spaced pattern.

In accordance with the principles of my invention in one illustrative embodiment thereof, my apparatus scans a series of two-dimensional images of spheres that have been illuminated with a structured light pattern and whose corresponding dioptric powers and depth coordinates are known. The process then filters the results of each scan of the image and takes its discrete Fourier transform, using a combination of band pass and analytic filters to suppress all side lobes and negative spatial frequencies in the Fourier spectrum, except for the components centered about the fundamental frequency. Next the inverse tangent of the quotient of the imaginary and real portions of the inverse transform is computed to obtain the instantaneous spatial phase for the pattern from each image. The instantaneous spatial phase is differentiated using the two point difference numerical approximation for example to obtain each pattern's instantaneous spatial frequency. Using a linear least-squares curve fitting technique, a polynomial is found that maps the instantaneous spatial frequencies for the patterns to the known dioptric powers of the spheres. The polynomial is then used to relate the instantaneous spatial frequencies obtained from a similar processing of a corneal image being examined to the instantaneous dioptric powers of its surface.

GENERAL DESCRIPTION

A uniformly spaced pattern can be made to appear on an idealized object in several ways. If the object is planar and diffuse, a uniformly spaced pattern will appear on the object by projection from a mask which itself has a uniformly spaced pattern. If the object is spherical and diffuse, such a mask will cause the pattern appearing on the more remote portions of the sphere to be somewhat more widely spaced apart than those portions that are nearer to the light source. If the object is spherical and specular, a uniformly spaced pattern can be obtained by reflection from a specially constructed illuminated mask.

In general, for both types of surfaces, the spacing between the light bands appearing on the object will tend to be greater over those portions of the object's surface which are more distant from the mask source. Conversely, the number of light bands per unit dimension of the surface generally decreases. Defining the number of light bands per unit dimension of the surface as the "spatial frequency" of the light pattern, it follows that spatial frequency decreases with increasing distance from the mask source and with decreasing slope or curvature for a specular object.

Where the height dimension of the surface causes the surface to be nearer or further from the mask source the spatial frequency of the light pattern will be generally higher over those surface portions that are closer to the light source and generally lower in those portions that are further away. Thus, where the structured light pattern is caused to appear on a corneal surface, the apical area which may be expected to have the highest dimensions of the corneal surface may be expected to exhibit a higher spatial frequency than the limbal region, however, the apical region is flatter, thus reducing the observed spatial frequency.

Figure 1:
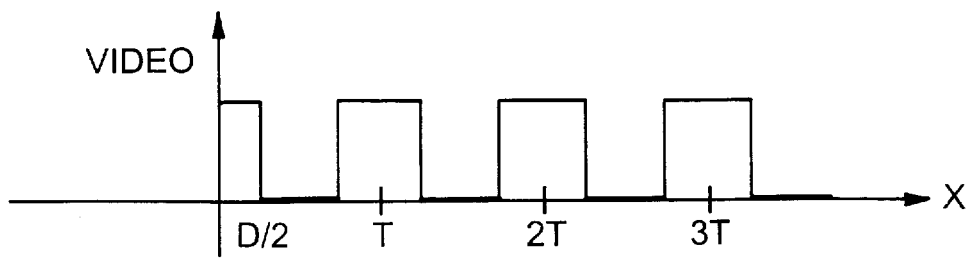
FIG. 1 is an idealized plot of video intensity versus distance obtained in orthogonally scanning the two-dimensional image of a uniformly spaced mire pattern appearing on a three-dimensional surface.
Figure 2:
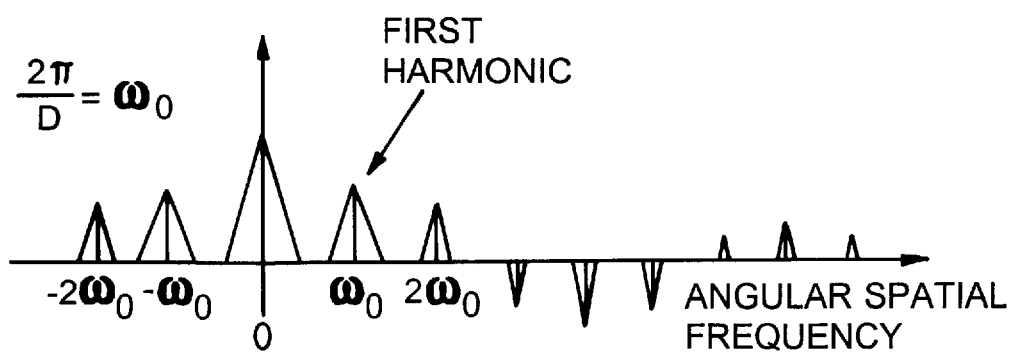
FIG. 2 is the Fourier transform of FIG. 1.
Figure 3:
FIG. 3 the band-pass filtered transform of FIG. 2.

When the structured light pattern appearing on the cornea is orthogonally scanned, the waveform of video intensity versus orthogonal distance is more or less that of a "square wave", FIG. 1, whose instantaneous frequency mimics the instantaneous spatial frequency of the light pattern. Thus, where variations in the surface height cause distortions in the light pattern, variations in the instantaneous spatial frequency will be produced. Using a fast Fourier transform algorithm (hereafter, FFT) to effect a discrete. Fourier transform of the video waveform produces a spectrum which includes positive and negative frequencies, FIG. 2. The Fourier spectrum of the orthogonally scanned image is next band-pass filtered and passed through an analytic filter to suppress all negative frequency components and reject all harmonics in the spectrum except the narrow band of frequencies adjoining the fundamental spatial frequency, FIG. 3. When the inverse transform is taken, the complex "analytic" signal, i.e., one having real components and imaginary components is obtained. The real component, $R(x)$, of the inverse transform has the form $$R(x)=A(x) \cos (\omega_0 x+\theta(x)) \tag{1}$$

while the imaginary component has the form $$I(x)=A(x) \sin (\omega_0 x+\theta(x)). \tag{2}$$

Figure 4:
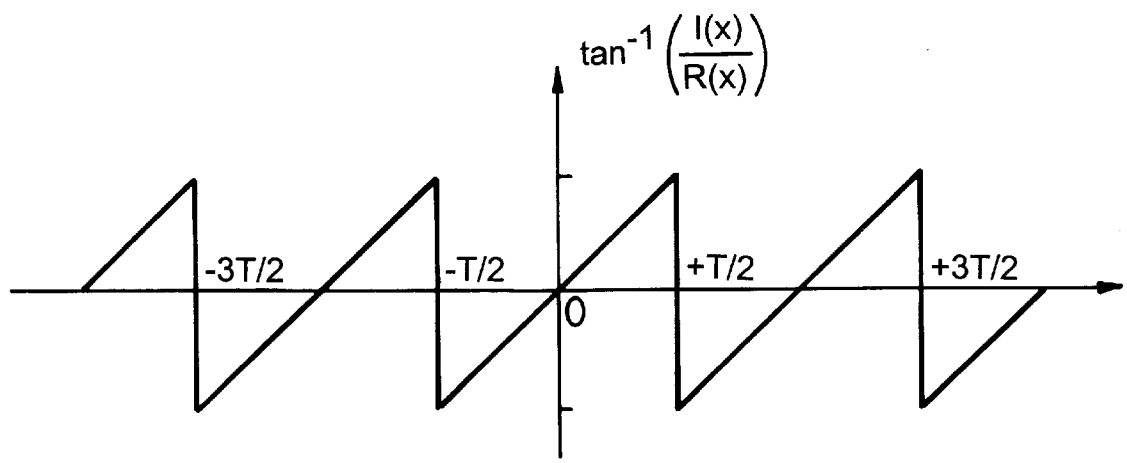
FIG. 4 is an idealized plot of the instantaneous spatial phase, i.e., the $\tan^{-1}$ of the quotient of the imaginary and real portions of the result of analytically filtering the waveform of FIG. 2 and then taking its inverse transform.
Figure 5:
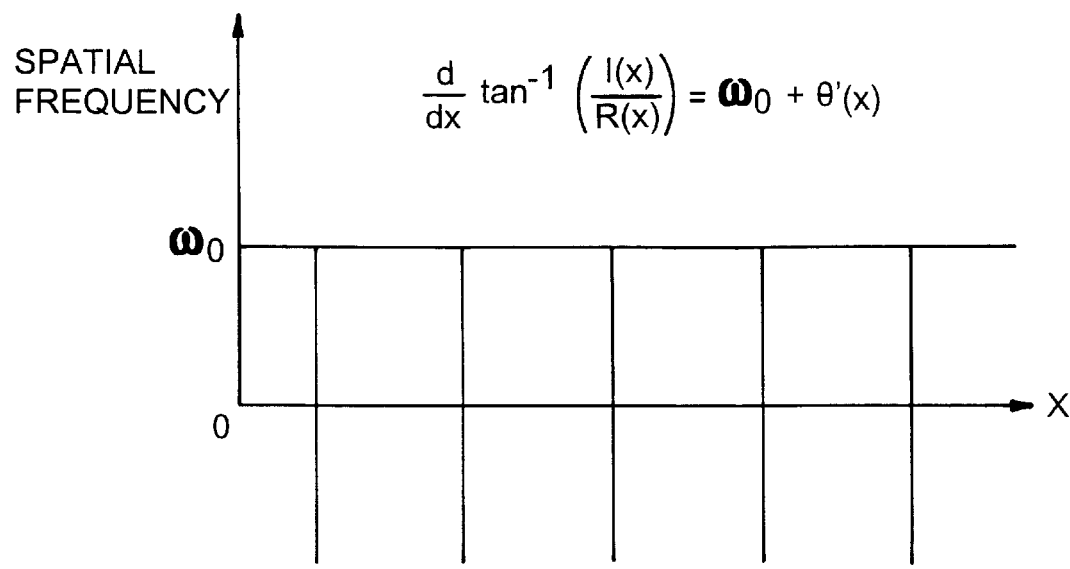
FIG. 5 is the instantaneous spatial frequency before removing discontinuities.
Figure 6:
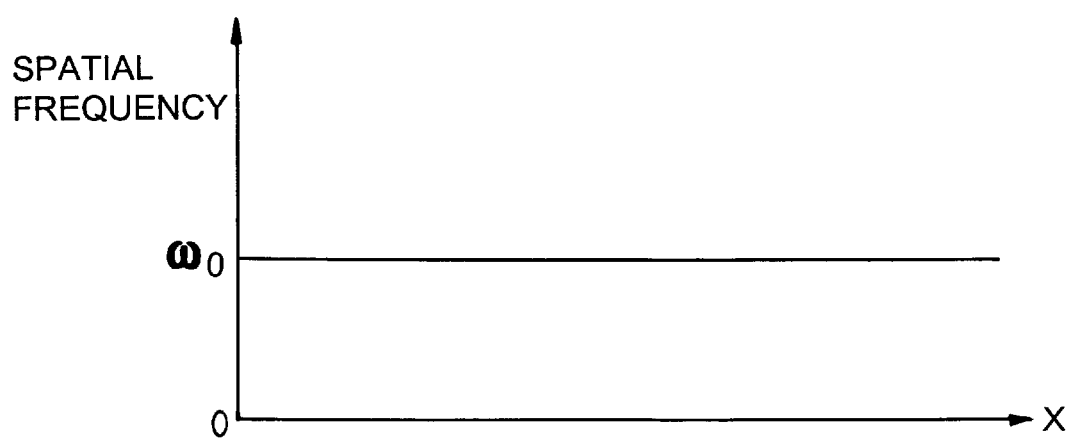
FIG. 6 is the instantaneous spatial frequency obtained for a planar object or for a spherical object on which equally spaced mires appear.
Figure 7:
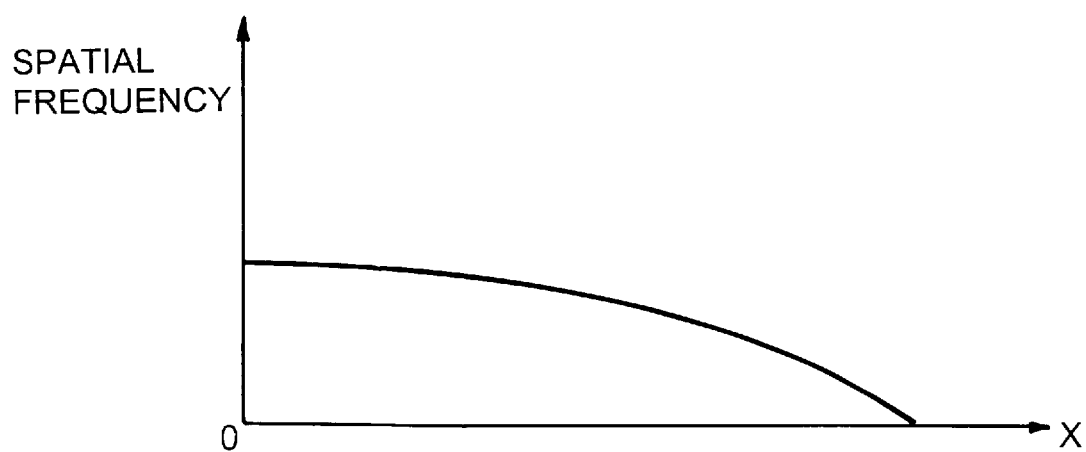
FIG. 7 is the instantaneous spatial frequency obtained for a spherical object using a mask having a uniformly spaced pattern.
Figure 8:
FIG. 8 is a plot of instantaneous frequency versus orthogonal surface distance.
Figure 9:
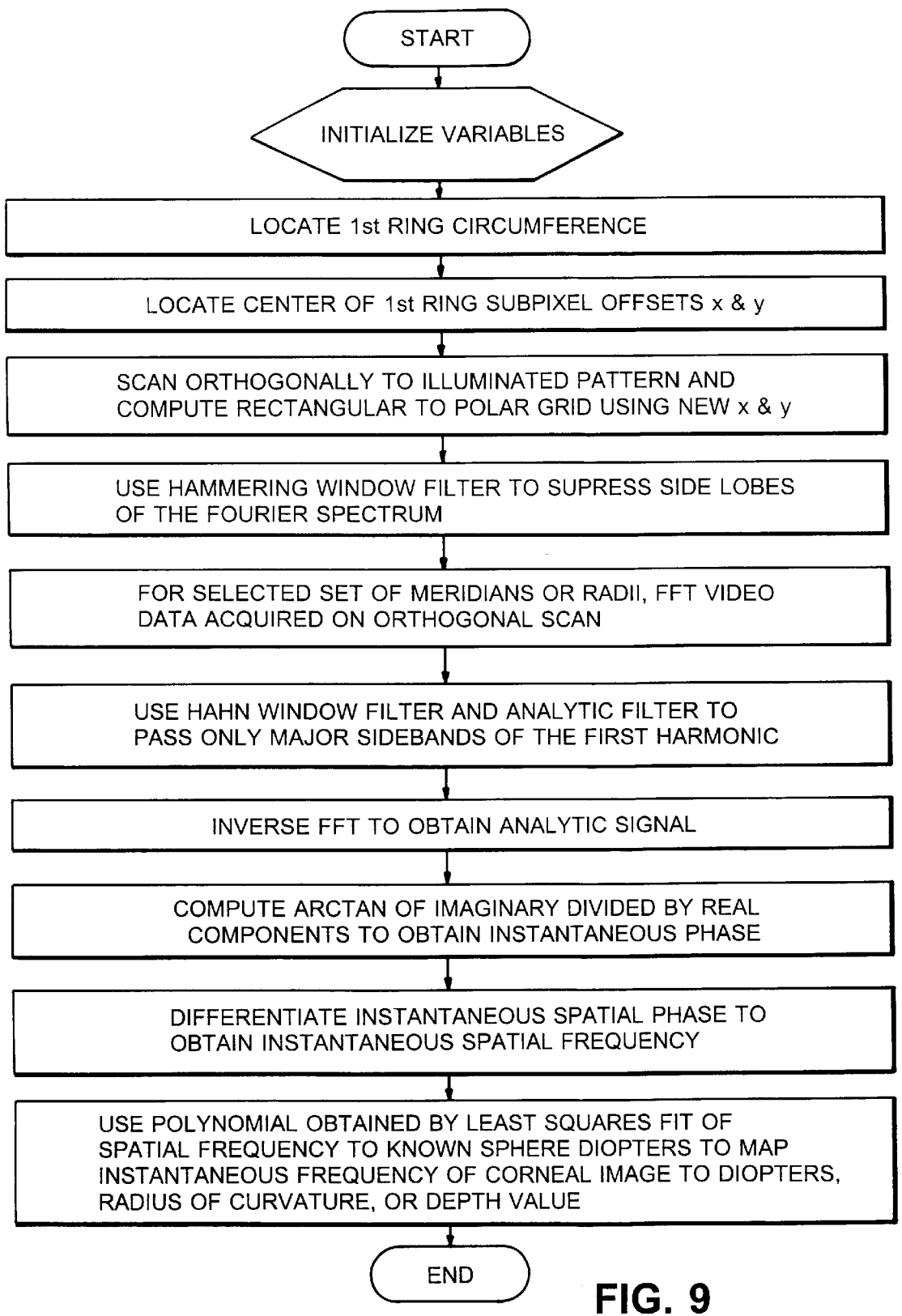
FIG. 9 is a flow chart of the processing steps performed in my invention.

Taking the inverse tangent of the quotient of the imaginary component divided by the real component $$\tan^{-1}\left(\frac{I(x)}{R(x)}\right), = \omega_0 x + \theta(x) \tag{2a}$$

yields the instantaneous spatial phase which, from equations (1) and (2) is seen to be a function of x. The instantaneous phase is a saw-tooth or ramp-like function having discontinuities every $2\pi$ radians, FIG. 4. The derivative $$f(x) = \frac{d}{dx} \tan^{-1}\left(\frac{I(x)}{R(x)}\right) = \omega_0 + \theta'(x) \tag{2b}$$

of the instantaneous phase waveform is the instantaneous frequency which also has discontinuities every $2\pi$ radians, FIG. 5 (variations in the instantaneous frequency not shown, but see FIG. 8 where these variations are shown.). The discontinuities are detected and eliminated by numerical interpolation as described, for example, in the article by Mitsuo Takeda, Hideki Ina and Soiji Kobayashi entitled "Fourier-transform method of fringe-pattern analysis for computer-based topography and interferometry", published in J. Opt Soc. Am, vol. 72, no. 1, January 1982 at pp. 156–160, see also, the article by Jose M. Tribolet, entitled "A New Phase Unwrapping Algorithm", published in the IEEE Transactions on Acoustics, Speech, and Signal Processing, vol ASSP-25, No. 2, April 1977, pp.170–177, to derive a smooth curve of the instantaneous spatial frequency, as shown in FIG. 6 for a planar object (or for a perfectly spherical object upon which a special mask has been used to project an equally-spaced pattern. FIG. 7 shows the smooth variation in instantaneous frequency for a spherical object upon which a pattern having a smoothly varying spacing has been produced using a mask having an equally spaced pattern. Any departure from the expected uniform spatial frequency in the case of FIG. 6, or from the smoothly varying spatial frequency in the case of FIG. 7, is relatable to a deviation in topography of the object. FIG. 9 is the overall flow chart for the process of my invention, the detailed coding for which is shown in the Appendix.

1. Diffuse Surface

The magnification effect produced by a projection lens is derivable from the lens equation. The lens equation relates the distance between the lens and the photographic plate (or mask) and the distance between the lens and the image which it focuses on a planar surface to the focal length of the lens. If the mask is a distance $d_0$ from the lens and if the planar surface is at a distance $d_f$ from the lens whose focal length is f, $$1/d_0+1/d_f=1/f \tag{3}$$

and the magnification is $$M = d_I/d_O. \qquad (4)$$

If the distance $d_O$ is fixed, the magnification depends on distance $d_I$. Thus, as the planar surface is moved away from the lens the size of the image increases. If the illuminated object consists of a pattern of alternating black and white stripes, as the image increases in size the number of stripes per unit dimension of the planar surface decreases. The number of stripes per unit length or line pairs per millimeter of a optical pattern is called the spatial frequency. If the spatial pattern is periodic, with a period T, then it can be decomposed into its Fourier series. Thus, for a periodic pattern of bars having width D and period T, the Fourier expression for the pattern is that of a periodic function, $f_p$, of x, i.e., $$f_p(x) = \sum_{i=0}^{\infty} a_i \cos(i\omega_o x) + b_i \sin(i\omega_o x), \qquad (5)$$

where $$\omega_o = \frac{2\pi}{T}, \qquad (6)$$

$$a_i = \frac{\sin(i\omega_o D/2)}{i\omega_o T/2}, \text{ and} \qquad (7)$$

$b_i=0$ (where the pattern is symmetrical about the origin). The image will have a spatial frequency which, for a diffuse object, is proportional to the magnification predicted by the lens equation for a projection lens.

In accordance with my method, the fundamental spatial frequency $f_1$ is determined and converted to either the surface height $D_1$, by polynomial curve fitting, i.e., $$D_1 = g(f) = A_0 + A_1 f + A_2 f^2 + \ldots + A_n f^n, \qquad (8)$$

or to magnification M, i.e., $$M = B_0 + B_1 f + B_2 f^2 + \ldots + B_n f^n. \qquad (9)$$

If the pattern is projected onto a non-planar object the discrete bar spectra become individual "bell"-shapes. The local spatial frequency varies with position. This varying spatial frequency is called the instantaneous or local spatial frequency.

The instantaneous frequency variation in an image obtained from a three-dimensional object is generally not periodic, it varies with the depth of the object for a diffused imaging system or with the depth and curvature for a specular imaging system. Thus, if the object is a human cornea, the depth or height of the surface may be approximated by the following equation, i.e., $$y^2 = 2R_o x - \mu x^2, \qquad (10)$$

or, equivalently $$x = R_o - \frac{\sqrt{(R_o)^2 - \mu y^2}}{\mu}, \qquad (11)$$

where $R_O$ is the apical radius of the "average" human cornea, $R_0=7.58$ mm; $\mu$ is the shape factor, $\mu=1$ for sphere and $\mu=0.85$ for the human cornea; x=depth of cornea; and y=radius from apex to limbus. (Note, it is "y" rather than "x" in Mendel's equation (10) and in equation (11) which corresponds to "x" in equations (1), (2) and (5)).

The equation of a one-dimensional radial slice, FIG. 7, through the object, e.g., the cornea, which reveals its profile or surface contour as a function of corneal depth, x, is the pattern function P(y). The pattern function P(y) will be distorted by a magnification, M(x), which depends on x, and since x is given by equation (11), P(y) becomes $$P(y) = P(Mx) = P\left(M \frac{(R_o - \sqrt{(R_o)^2 - \mu y^2})}{\mu} y\right). \qquad (12)$$

The spectrum about the fundamental frequency in this case is widened by the spatially varying magnification. The analytic signal can be obtained by taking the FFT of the input signal and band-pass filtering around the positive fundamental frequency, then taking the inverse FFT, i.e., $$H\{P(y)\} = A(y) e^{j\frac{M}{\mu}(R_o - \sqrt{(R_o)^2 - \mu y^2})y}, \qquad (13)$$

where A(y) is the amplitude variation due to variations in illumination. The resulting complex waveform is the desired analytic signal. The actual surface can be obtained by taking the inverse tangent of the quotient of the imaginary and real parts of the analytic signal.

2. Specular Surface Considerations

Where the surface to be mapped is specular, the direction taken by a ray reflected from a point on the surface depends not only on the distance between the surface and the mask source but also on the angle between the incident ray and the normal to the surface at the point in question. The complex calculations of ray direction is avoidable, however, by exposing a series of standard size specular spheres to a given mask. Then, using the above-described Fourier transform and filtering technique, the corresponding array of spatial frequencies is obtained. The spatial frequencies so obtained are tabulated against sphere diameters (which are related to the diopters of refraction for the cornea of corresponding diameter). From the table the coefficients are found for a polynomial $$D_1 = A_0 + A_1 f + A_2 f^2 + \ldots A_n f^n \qquad (14)$$

(using linear least squares technique) which maps the instantaneous frequencies to diopter values.

3. Details on Processing

The main program for my invention is identified as "program compute_corneal_power" set forth in the Appendix in the Pascal language. In the radial scanning of the video image which precedes the steps of taking the Fourier transform it is advantageous to begin the scanning, as described at column 8, line 9 et seq. of the aforementioned Gersten, et al. U.S. Pat. No. 4,863,269, at a center point determined from the first ring pattern appearing in the image. (See the step in the main program "find_first_ring (ring1)".) In accordance with the present invention, this is the only ring pattern whose "edges" need to be determined.

In scanning certain images it may be found desirable to avoid reading data adjacent the aforementioned center point. However it is unwise to present discontinuities of the phase of the data as applied to the Fourier transform steps. Accordingly, while I prefer to eliminate data within a small radius adjacent the center point, I do not leave a gap in the data presented to the Fourier transform. Instead, I present the data from two radial scans lying 180 degrees apart as being from one meridian, joining the data lying on opposite sides of the circle of omitted data. This is done in the procedure "sample_meridian" called for in the main program and described in detail in the Appendix. As noted in the main program, after the Fourier transform steps are performed, the center is restored (see "procedure restore_center" in the Appendix) and the dioptric powers obtained from the processing are plotted in their correct positions.

The plotting programs used in the above-mentioned Gersten et al. patent device plotted the dioptric powers of the surface along the perimeter of the rings observed in the image. My present invention provides instantaneous dioptric powers over the entire image. To use these prior plotting programs a "ring structure" is necessary. Accordingly, the step entitled "compute_spatial_freq_pseudo_rings" creates pseudo rings from which the instantaneous dioptric information generated by my present invention can be read and delivered to the plotting programs. As shown in FIG. 8, a "ring" for such plotting is identified by taking the mean value of eight instantaneous frequencies read along a meridian.

Accordingly, I have described an illustrative embodiment of my invention. Numerous modifications may be employed by those skilled in the art such as substituting a converging for the diverging lens in which case "minification" substitutes for the magnification which has been described. In addition, other types of windows may be substituted for the Hamming and "hanning" windows set forth in the described embodiment. Alternative transforms, such as the Hilbert transform or finite impulse response filters may also be employed to derive the instantaneous spatial frequencies and other forms of polynomial curve fitting may be employed besides the linear least-squares technique described. Moreover, although the use of the instantaneous spatial frequencies has been described, it may be advantageous when mapping a diffuse surface to omit the step of converting the instantaneous spatial phase to frequency and, instead, especially where the illuminating rays are applied at an angle to the surface, such as in the aforementioned Warnicki patent operating microscope apparatus, to map the instantaneous spatial phase directly to spherical radii instead of to diopters. Many such substitutions may be made without, however, departing from the spirit and scope of my invention.

APPENDIX

```
program compute_corneal_power;
uses
    crt,deplib,filtlib,ring1lib,plotlib,vgalib,pointlib,
    cmplxlib,cmplxvs,fftlib,v8lib,util1,global;
const
    debug = true;
var
    ix1,iy1: integer;
    max_diop,min_diop: single;
    exam: words;
begin
    if paramcount = 1 then exam := paramstr(1) else exit;
    new(meridian);
    new(dio);
    fillchar(dio^,sizeof(dio^),0);
    set_rick_defaults(ix1,iy1,ham_window,han_window);
    x_ctr := ix1;
    y_ctr := iy1;
    display_selected_frame(exam,error);
    find_the_fixation_light(x_ctr,y_ctr,vga_xc,vga_yc);
    find_first_ring(ring1);
    find_offsets(ring1,xmean,ymean);
    for itheta := 0 to 127 do
        begin
            sample_meridian (debug, ring1, itheta, -xmean,
                -ymean, ham_window, meridian, last_points);
            rfftc(meridian^,m);
            fft_filter(debug,meridian,han_window);
```

APPENDIX-continued

```
            fftc(meridian^,m,invs);
            compute_phase(debug,itheta,meridian,ring1,phase);
            restore_center(itheta,ring1,meridian);
            compute_spatial_freq_pseudo_rings (debug, itheta,
                phase, dio);
            compute_powers(itheta,min_drop,max_diop,dio);
            write(itheta:4);
        end;
    lowpass_meridians(last_points,dio);
    lowpass_circumference(dio);
    lowpass_circumference(dio);
    preen_output(dio);
    write_output_to_disk(min_diop,max_diop,dio);
    dispose(meridian);
    dispose(dio);
end.
procedure sample_meridian(debug: boolean; ring1: r256; itheta:
    integer; xmean,ymean: single; hw: r512a; var mer: r512c; var
    last_points: i256);
var
    iphe,ipix,ir,offr0,offr1,lp0,lp1: integer;
    f,theta: single;
    vid: i512;
    curv: ^r512a;
begin
    fillchar(mer^,sizeof(mer^),0);
    fillchar(vid,sizeof(vid),0);
    for ir := 1 to last do
        read_polar_pixel(ir,itheta,2.0*xmean,2.0*ymean,vid[ir]);
    for ir := 0 to last-1 do
        read_polar_pixel(ir,itheta+128,xmean,ymean,vid[-ir]);
    if itheta = 0 then
        for iphe := 0 to lim do
            load_last_points(iphe,vid,last_points);
    lp0 := last_points[itheta];
    lp1 := last_points[itheta+128];
    for ir := 0 to lp0 do
        begin
            offr0 := round(ring1[itheta]);
            offr1 := round(ring1[itheta+128]);
            mer^[ir].r    :=    vid[ir+offr0]    *
                hw[ir+(last_rad-lp0)];
            mer^[-ir+1].r    :=    vid[-ir-offr1]    *
                hw[-ir-(last_rad-lp1)];
        end;
    if debug then
        begin
            new(curv);
            for ir := -last+1 to last do
                curv^[ir] := mer^[ir].r;
            plot_r512a(curv^,13,6,true);
            dispose(curv);
        end;
end;
procedure restore_center(itheta: integer; ring1: r256; var
    meridian: r512c);
var
    ir: integer;
begin
    for ir := last downto round(ring1[itheta]) do
        begin
            meridian^[ir]    :=    meridian^[ir-round    (ring1
                [itheta])];
            meridian^[-ir+1]    :=    meridian^[-ir+round    (ring1
                [itheta])+1];
        end;
    for ir := -round(ring1[itheta]+1) to round(ring1[itheta]) do
        begin
            meridian^[ir].r := 0.0;
            meridian^[ir].i := 0.0;
        end;
end;
```

What is claimed is:

1. In the process of displaying a two-dimensional map identifying the third dimension of a three-dimensional specular surface illuminated with a mire pattern by processing a two-dimensional image of said illuminated surface, the improvement comprising the steps of:

a. orthogonally scanning said mire pattern as it appears in the images of three-dimensional specular spheres having known spherical radii to produce a two-dimensional scanned image for each of said spheres, b. processing each said two-dimensional scanned image to ascertain the instantaneous spatial frequencies contained therein, c. tabulating said instantaneous spatial frequencies to obtain the coefficients defining a polynomial relating said spatial frequencies to the known spherical radii of said spheres, d. orthogonally scanning said mire pattern as it appears in the image of an unknown three-dimensional quasi-spherical specular surface illuminated with said mire pattern to produce a two-dimensional scanned image corresponding to said unknown surface, e. processing said scanned image corresponding to said unknown surface to ascertain the instantaneous spatial frequencies contained therein, f. substituting said instantaneous spatial frequencies corresponding to said unknown surface in said polynomial to determine the third dimension of said unknown surface, and g. displaying a two-dimensional image map of said unknown surface having said third dimension identified therein.

2. In the process of claim 1, the improvement wherein the coefficients of said polynomial are obtained by employing the linear least squares technique to map said instantaneous frequencies to said radii of said known spheres.

3. In the process of claim 1, the improvement wherein said processing of said images to ascertain said instantaneous spatial frequencies includes taking a discrete transform of the results of said scanning.

4. The process of claim 3, the improvement wherein the results of said scanning are filtered prior to taking said transform and wherein said discrete transform is a Fourier transform producing a spectrum exhibiting determinable sidelobes.

5. The process of claim 4, the improvement wherein said processing to ascertain said instantaneous spatial frequencies includes multiplying the results of said scanning by a filtering window to reduce said sidelobes in said spectrum produced by said Fourier transform.

6. In the process of claim 5, the improvement wherein said window is a Hamming window.

7. In the process of claim 3, the improvement wherein said processing to ascertain said instantaneous spatial frequencies includes subjecting the results of said discrete transform to an analytic filter to pass only a portion of the spectrum thereof.

8. In the process of claim 7, the improvement wherein said processing to ascertain said instantaneous spatial frequencies includes taking an inverse transform of said portion passed by said analytic filter.

9. In the process of claim 8, the improvement wherein said processing to ascertain said instantaneous spatial frequencies includes taking the quotient of imaginary and real components of said inverse transform to obtain the instantaneous spatial phase.

10. In the process of claim 9, the improvement wherein said processing to ascertain said instantaneous spatial frequencies includes differentiating said instantaneous spatial phase.

11. In the process of claim 10 the improvement wherein said processing to ascertain said instantaneous spatial frequencies includes numerically eliminating discontinuities in said instantaneous spatial phase.

12. The process of displaying a map of the dioptric powers of refraction exhibited over an unknown, three-dimensional, quasi-spherical, specular surface, comprising the steps of:

a. processing a plurality of orthogonally scanned images of known specular spheres exhibiting a mire pattern to obtain the coefficients of a polynomial relating (i) the known dioptric powers of said plurality of spheres to (ii) the instantaneous spatial frequencies exhibited by said mire pattern in said images, b. processing an orthogonally scanned image of an unknown three-dimensional quasi-spherical specular surface illuminated with said mire pattern to ascertain the instantaneous spatial frequencies contained in said image, c. substituting said instantaneous spatial frequencies obtained from processing said image of said unknown surface in said polynomial to obtain the dioptric powers of said unknown surface, and d. displaying a two-dimensional map of the dioptric powers of said unknown surface on said image.

13. Processing in a stored program controlled apparatus the two-dimensional image of a three-dimensional surface illuminated with a structured light pattern to quantify the third dimension of said surface, comprising the steps of:

a. scanning, orthogonally to said pattern, the images of a plurality of three-dimensional surfaces, the third dimensions of which, at a plurality of predetermined points in said light pattern, are known;

b. processing each of said images to ascertain the local spatial phase at said predetermined points, c. mapping said local spatial phase ascertained at said predetermined points in said plurality of images to obtain the coefficients of a polynomial relating said local spatial phase in said plurality of images to the known third dimensions thereof, and d. substituting in said polynomial the local spatial phase of said predetermined points appearing in the image of an unknown surface to ascertain the corresponding third dimensions thereof.

* * * * *